United States Patent [19]

Horn et al.

[11] 4,328,000

[45] May 4, 1982

[54] QUANTITATIVE DETERMINATION OF THE SURFACE CHARGE OF SERUM LIPOPROTEINS

[75] Inventors: Dieter Horn, Heidelberg; Erik Lueddecke, Ludwigshafen; Claus C. Heuck, Wilhelmsfeld, all of Fed. Rep. of Germany

[73] Assignee: BASF Aktiengesellschaft, Fed. Rep. of Germany

[21] Appl. No.: 178,678

[22] Filed: Aug. 15, 1980

[30] Foreign Application Priority Data

Aug. 24, 1979 [DE] Fed. Rep. of Germany ....... 2934228

[51] Int. Cl.$^3$ ............................................. G01N 33/50
[52] U.S. Cl. .................... 23/230 B; 23/909; 424/7
[58] Field of Search .............. 23/230 B, 909, 902, 23/927; 424/7; 422/75, 61

[56] References Cited

U.S. PATENT DOCUMENTS

| | | | |
|---|---|---|---|
| 3,884,638 | 5/1975 | Dixon et al. | 23/230 B |
| 4,042,329 | 8/1977 | Hochstrasser | 23/230 B |
| 4,185,963 | 1/1980 | Heuck | 23/230 B |
| 4,211,530 | 7/1980 | Goverde et al. | 23/230 B |
| 4,211,531 | 7/1980 | Das | 23/230 B |

FOREIGN PATENT DOCUMENTS 2027195  2/1980  United Kingdom .

OTHER PUBLICATIONS

Heuck et al.; Clin. Chem. 23/3, (1977); pp. 536–540.
Nishida et al.; J. Biol. Chem. 245/18, (1970); pp. 4689–4697.
Progress Colloid and Polymer Sci. 65, (1978); pp. 251–264; Dr. Dietrich Verlag.
Biochemistry, vol. 12, Nr. 14, pp. 2645–2649, (1973).

*Primary Examiner*—Kenneth M. Schor
*Attorney, Agent, or Firm*—Keil & Witherspoon

[57] ABSTRACT

Disclosed is the polyelectrolytic titration of serum lipoproteins, the negative surface charge of the latter being determined quantitatively by adding an excess amount of a polycation in aqueous solution to the particular serum lipoprotein and then back-titrating the positive charge of the polycation, which has not been neutralized by the negative surface charge, against a chromotropic polyanion, in the presence of a metachromatic dye as the indicator. The method according is used for the diagnosis of lipometabolic disorders.

6 Claims, No Drawings

QUANTITATIVE DETERMINATION OF THE SURFACE CHARGE OF SERUM LIPOPROTEINS

The present invention relates to a polyelectrolytic titration of serum lipoproteins against a polycation.

It is known that 3 categories of lipoproteins, which are present in the form of particles, are detectable in human serum, namely very low density lipoproteins (VLDL), low density lipoproteins (LDL) and high density lipoproteins (HDL) which each have a different significance for the development of arteriosclerosis. Whilst VLDL and LDL promote atherogenesis, HDL are said to have a protective action. A metabolic relationship between the individual categories of lipoproteins exists in that individual constituents of the LDL, for example apolipoprotein B and cholesterol, or of the HDL, for example triglyceride or apolipoprotein A, originate from the VLDL and on biochemical degradation are transferred to the other category of lipoproteins.

It is also known that the composition of the individual lipoproteins from persons suffering from a primary or secondary lipometabolic disorder differs markedly from that of the lipoproteins from normolipemic persons. Only little is known of the specific chemical and physico-chemical surface characteristics of the individual categories of lipoproteins. Thus, inter alia, it has been found that the neuraminic acid content is raised in the LDL of persons suffering from type II hyperlipoproteinemia. This characteristic is of significance for the metabolism of the LDL. Furthermore, it has been concluded from electrophoretic investigations that VLDL from the serum of persons suffering from type IV hyperlipoproteinemia have a higher isoelectric point than VLDL from the serum of normolipemic persons.

A specific interaction between the lipoprotein surface and an enzyme, a cell membrane or connective tissue fibers is a prerequisite for the degradation or the deposition of lipids from serum lipoproteins. The bonding of lipoprotein to a lipase is in fact the reaction which determines the rate at which enzymatic degradation takes place. Phospholipids on the substrate surface can have diverse effects on the attack by various lipases, for example on a serum lipoprotein.

Various mechanisms are discussed which determine the depositon of lipoproteins in the vascular walls. According to the data available to date, the bonding of lipoproteins to elastin appears to take place via lipids positioned on the surface. In contrast, the bonding of lipoproteins to cell membranes or mucopolysaccharides is effected via basic groups in the protein constituent of the lipoprotein particle.

These obervations show that a change in the surface structure can have a decisive effect on the metabolism of the lipoproteins and thus on the synthesis of lipids. From the viewpoint of epidemiology and preventive medicine, these findings appear to be the more significant since data obtained hitherto have shown that increased serum concentrations of lipids and thus of specific lipoproteins are detectable as a consequence of a lipometabolic disorder. Numerous factors come into consideration as possible causes. The significance of the surface characteristics of lipoproteins has indeed been indicated by numerous investigations, but more accurate analyses have hitherto been carried out only to a limited extent, since the methods available hitherto for characterizing the structural elements of the lipoprotein surface have been inadequate.

In the field of colloid chemistry, colorimetric titration methods have recently been developed for the determination of polyelectrolyte molecules, cf., for example, Horn, D., Progress Colloid and Polymer Sci. 65, (1978) 251-264. These methods have also been used in isolated cases to measure cloudiness, in the quantitative determination of dissolved naturally occurring polymers, for example heparin, or semisynthetic polymers, for example methylglycol-chitosan. This quantitative method of determination for polyelectrolytes can also be used to measure polymer adsorption at interfaces of disperse particles. Before a determination of this type is carried out, the particles coated with a layer of adsorbed polymer must be separated from the polymer molecules which have not been adsorbed and have remained in the dispersant.

It has been disclosed that lipoproteins of human serum interact with polyanions, for example dextran sulfate, or polycations, for example polyethyleneimine (T. Nishida and U. Cogan, J. biol. Chem. 245, (1970), 4689-4697; Heuck et al. Clin. Chem. 23, (1977), 536-540). These reactions have been used for fractionating lipoprotein from human serum. Quantitative data on the surface charge of lipoproteins cannot be obtained by this method.

It is an object of the present invention to develop a method for the quantitative determination of the negative surface charges of serum lipoproteins in order thus to obtain more accurate data on factors which play a role in the pathogenesis of lipometabolic disorders. This object is achieved by providing a polyelectrolytic titration of the serum lipoproteins against a polycation.

We have found a method for the quantitative determination of the negative surface charge of serum lipoproteins, wherein a defined excess amount of a polycation in aqueous solution is added to the particular serum lipoprotein and the positive charge, of the polycation, which has not been neutralized by the negative surface charge is back-titrated against a chromotropic polyanion in the presence of a metachromatic dye as the indicator.

The polycation used in the method according to the invention is bonded to the polyanionic interface of the lipoproteins present. The negative surface charge of the lipoprotein is given by the difference between the initial free charge on the polycation and the free charge determined by back-titration.

The method according to the invention allows measurements to be carried out in a surprisingly simple manner and with high accuracy, since the surface charge of the lipoproteins to be tested is determined down to a range of $10^{-8}$ equivalent/ml of solution. A further advantage is that the measurements are carried out directly in the solution of the lipoprotein serum fraction.

The lipoproteins to be determined, especially the categories VLDL, LDL and HDL, are as a rule obtained in the form of a serum fraction from human serum by ultracentrifuging in a conventional manner (GIT Fachz. Lab. 23, (1979) 748-753).

A defined excess amount of a polycation in aqeous solution is then added to the serum fraction containing the lipoprotein. The polycation is bonded to negatively charged residues at the lipoprotein surface.

Suitable polycations are cationic polymers, eg. polyethyleneimine, modified polyethyleneimines or polydiallyldimethylammonium salts, especially the chlorides.

The polycation which is particularly preferred is polyethyleneimine. A suitable polyethyleneimine to be used according to the invention has a weight-average molecular weight, determined by light scattering, of from 1,000 to 5 million (corresponding to a K value of from 14 to 31), preferably of from 20,000 to 30,000, and an intrinsic viscosity of from 7.0 to 9.5 ml/g. A particularly suitable polyethyleneimine is obtainable under the tradename Polymin G500.

The cationic charge density of the polyethyleneimine depends on the pH and is advantageously 21 milliequivalent/g at pH 3, 18 milliequivalent/g at pH 5, 15 milliequivalent/g at pH 7 and 12 milliequivalent/g at pH 9.

Advantageously, aqueous standard solutions which contain from 1 to 10 mg, preferably from 2.0 to 6 mg, of polyethyleneimine per liter are used.

A particularly suitable polydiallyldimethylammonium chloride is obtainable under the name Cat-floc 261.

In principle, any chromotropic polyanion can be used for the back-titration. Advantageous chromotropic polyanions are the alkali metal salts, in particular the potassium or sodium salts, of polyvinyl sulfates having a degree of esterification of from 30 to 100%, polyphosphates, dextran sulfates, polyvinyl alcohol sulfates having a degree of esterification of about 50%, heparin, chondroitin sulfates, polyacrylates and polymethacrylates in the form of their aqueous solutions.

The preferred polyanion is potassium polyvinylsulfate (PVSK).

A suitable PVSK has a weight-average molecular weight, determined by light scattering, of from 1,000 to 30,000 and advantageously has a degree of esterification of 100% and a charge density at pH 7 of about 6 milliequivalent/g.

Standard solutions which contain from 100 to 1,000 mg/l, preferably from 300 to 400 mg/l, are advantageously used.

The excess polycation is back-titrated in the presence of a metachromatic dye, which also has a positive charge, as the indicator. Examples of suitable indicators are pyronine G, acridine orange, methylene blue or toluidine blue, o-toluidine blue being particularly preferred.

As a rule, the indicators are used in the form of an aqueous stock solution having a concentration of about 40 mg/l. About 3 ml of this solution are used per 100 ml of reaction medium, so that the indicator concentration during the determination is as a rule from $10^{-7}$ to $10^{-5}$ mole/l.

The end point is advantageously determined colorimetrically, using equipment as described, for example, in Progress Colloid and Polymer Sci. 65, (1978) 251–264.

The titration is advantageously carried out at room temperature and at a pH of from 3.5 to 9, preferably from 6 to 8.

It should be emphasized that low molecular weight ions, inorganic salts, monobasic, dibasic and tribasic acids, monoacidic, diacidic and triacidic bases and organic ions, and in particular ammonium salts, do not interfere if present in an amount less than about $10^{-2}$ mole/l.

For this reason, the method according to the invention can also be carried out in the presence of sodium chloride or, if necessary, of buffer solutions, for example of a phosphate buffer, and in this case the salt concentration should not exceed a value of $5 \times 10^{-2}$ mole/l.

The actual titration is advantageously carried out in an automatic apparatus as described, for example, in the literature reference mentioned above, and as a rule is carried out in dosage steps of 0.01 ml, in a conventional manner, until the end point of the indicator used is reached.

By means of the method according to the invention for the determination of the surface charge of lipoproteins, it is possible to obtain differetiated evidence with regard to the surface characteristics of these particles. This evidence is of particular importance with respect to the catabolism of lipoproteins and the bonding of lipoproteins to cell membranes and vascular walls, since, in the development of arteriosclerosis, a causal relationship has been established between the surface characteristics of lipoproteins in human serum and the deposition of lipids in the vascular walls.

EXAMPLE 1

1 ml of a fraction containing from 0.5 to 20 mg of lipoprotein is added to 100 ml of a solution containing 0.4 mg of polyethyleneimine (PEI)/100 ml, at 23° C. and at a pH of 7, and the mixture is stirred for 15 minutes.

3 ml of a stock solution containing 40 mg of toluidine blue per liter are then added as the indicator (final concentration of 1.2 mg/l corresponds to $4 \times 10^{-6}$ mole/l) and the solution is titrated against a PVSK solution having a concentration of 0.324 g/l ($2 \times 10^{-3}$ mole/l).

The titration is carried out in an automatic apparatus of the type described in Progress Colloid and Polymer Sci. 65, (1978) 251–264, in dosage steps of 0.01 ml until the end point of the indicator is reached, at a wavelength of 635 nm.

The parameter to be determined, i.e. the negative surface charge per unit quantity (g) of lipoprotein, is calculated from the difference between the number of free cationic centers in the PEI initially added and the number of such centers back-titrated, for a known charge density of 14.7 milliequivalent/g of polyethyleneimine and of 6.17 milliequivalent/g of PVSK.

To increase the accuracy, it is advantageous to measure the consumption of polyethyleneimine by the lipoproteins in a titration series using increasing amounts of lipoprotein. The relationship between the consumption and the amount of lipoprotein employed is linear and the charge density per unit weight can be determined from the gradient of the straight line.

The calculation to obtain the specific charge density per unit surface area (milliequivalent/$m^2$) is carried out after determining the specific surface area of the lipoproteins by measuring the particle size distribution of the samples by known methods. Suitable methods are ultracentrifuging, analysis by electron microscopy or, advantageously, photon correlation spectroscopy. The latter method permits direct measurement of the translational diffusion coefficients of the lipoproteins (R. W. De Blois, E. E. Uzgiris, S. K. Devi and A. M. Gotto jr., Biochemistry 12, (1973) 2645–49), and using the autocorrelation/time function, which can be determined experimentally, of the intensity of laser light scattered at the samples, the so-called Z-mean and the variants of the diffusion coefficient are obtained, in accordance with the method of D. E. Koppel, J. Chem. Phys. 57, 4841–4820 (1972). These values are used to calculate the third moment of the radius distribution, and from this the specific surface area (per unit volume) of the lipoprotein samples is obtained direct.

EXAMPLE 2

Using the same procedure as in Example 1, 1 ml of a fraction containing from 0.5 to 20 mg of lipoprotein is added to 100 ml of a solution containing 2.2 mg of Catfloc 261/100 ml, at 23° C. and a pH of 7, and the mixture is stirred for 15 minutes.

The parameter to be determined, i.e. the negative surface charge per unit quantity (g) of lipoprotein, is calculated from the difference between the number of free cationic centers in the Catfloc initially added and the number of such centers back-titrated, for a known charge density of 2.63 milliequivalent/g of Catfloc.

The Table which follows gives the test results obtained by measuring the specific surface charge of lipoproteins obtained from persons suffering from various forms of hyperlipoproteinemia. The surface charge was measured as indicated in the Examples. The specific surface area was calculated with the aid of the photon correlation spectroscopy measurement.

On the basis of an investigation carried out using lipoproteins isolated from donors with normolipemia and from donors suffering from various forms of hyperlipoproteinemia (types IIa, IIb, III, IV and V according to Frederickson) it was found that the negative charge density of the surface of LDL is lower than that of VLDL (Table 1). The investigation also showed that there are relatively large variations in the negative charge density of the surface of VLDL and there is no significant correlation to the size of the particles or, surprisingly, to their phospholipid content. On the other hand, there is a positive correlation to the content of apolipoprotein B in the VLDL, a close relationship between this content and the development of arteriosclerosis having been established in numerous investigations.

The clinico-chemical value of the information to be obtained with the aid of the newly developed method appears to be the more significant since it is possible, by a simple measurement procedure, to determine causal factors for the degradation or the deposition of lipoproteins in the vascular walls, for example to determine the electrostatic properties of lipoproteins for the purpose of the clinical differential diagnosis of primary and secondary lipometabolic disorders.

TABLE 1

| Example | Sample | Polycation | Polyanion | Lipoprotein (mg/ml) | Negative surface charge/volume (milliequivalent/ml) | Lipoprotein diameter ($\mu$m) | Variance | Specific surface area ($m^2/cm^3$) | Specific surface charge (milliequivalent/ml) |
|---|---|---|---|---|---|---|---|---|---|
| 1 | LDL | PEI | PVSK | 4.6 | $1.666 \times 10^{-3}$ | 0.0300 | 0.282 | 420 | $0.862 \times 10^{-3}$ |
| 2 | LDL | " | " | 3.39 | $1.24 \times 10^{-3}$ | 0.0306 | 0.312 | 480 | $0.762 \times 10^{-3}$ |
| 3 | LDL | Catfloc 261 | " | 2.99 | $0.32 \times 10^{-3}$ | 0.0558 | 0.884 | 719 | $0.147 \times 10^{-3}$ |
| 4 | VLDL | PEI | " | 2.21 | $1.47 \times 10^{-3}$ | 0.0472 | 0.298 | 281 | $2.368 \times 10^3$ |
| 5 | VLDL | " | " | 6.52 | $1.078 \times 10^{-3}$ | 0.0565 | 0.161 | 166 | $0.997 \times 10^{-3}$ |
| 6 | VLDL | " | " | 7.15 | $1.686 \times 10^{-3}$ | 0.0829 | 0.260 | 145 | $1.629 \times 10^{-3}$ |
| 7 | VLDL | " | " | 7.42 | $1.617 \times 10^{-3}$ | 0.0629 | 0.250 | 186 | $1.170 \times 10^{-3}$ |
| 8 | VLDL | " | " | 3.40 | $1.029 \times 10^{-3}$ | 0.0657 | 0.339 | 218 | $1.388 \times 10^{-3}$ |
| 9 | VLDL | " | " | 1.82 | $0.625 \times 10^{-3}$ | 0.0566 | 0.233 | 188 | $1.827 \times 10^{-3}$ |
| 10 | VLDL | " | " | 3.15 | $1.323 \times 10^{-3}$ | 0.0602 | 0.369 | 257 | $1.632 \times 10^{-3}$ |
| 11 | VLDL | " | " | 7.44 | $2.45 \times 10^{-3}$ | 0.0492 | 0.214 | 217 | $1.518 \times 10^{-3}$ |
| 12 | VLDL | " | " | 5.58 | $1.47 \times 10^{-3}$ | 0.0639 | 0.137 | 138 | $1.909 \times 10^{-3}$ |
| 13 | VLDL | " | " | 14.00 | $2.47 \times 10^{-3}$ | 0.0779 | 0.307 | 170 | $1.037 \times 10^{-3}$ |
| 14 | VLDL | Catfloc-261 | " | 2.15 | $0.16 \times 10^{-3}$ | 0.0475 | 0.168 | 201 | $0.366 \times 10^{-3}$ |
| 15 | Chylomicrons | PEI | " | 7.68 | $0.744 \times 10^{-3}$ | 0.1257 | 0.279 | 100 | $0.968 \times 10^{-3}$ |

We claim:

1. A method for the quantitative determination of the negative surface charge of serum lipoproteins, wherein the negative surface charge of the particular serum lipoprotein is neutralized by a defined excess amount of a polycation in aqueous solution and the excess amount of positive charges of the polycation is back-titrated against a chromotropic polyanion, in the presence of a metachromatic dye as the indicator.

2. The method of claim 1, wherein the polycation added is polyethyleneimine, modified polyethyleneimine or a polydiallyldimethylammonium salt in aqueous solution.

3. The method of claim 1, wherein the polycation added is a polyethyleneimine having a K value of from 14 to 31 in aqueous solution.

4. The method of claim 1, wherein the lipoprotein is a very low density lipoprotein (VLDL).

5. The method of claim 1, wherein the lipoprotein is a low density lipoprotein (LDL).

6. The method of claim 1, wherein the lipoprotein is a high density lipoprotein (HDL).

* * * * *